(12) United States Patent
Jaspart

(10) Patent No.: US 10,736,907 B2
(45) Date of Patent: Aug. 11, 2020

(54) USE OF SUGAR-ALCOHOLS IN TIBOLONE COMPOSITIONS

(71) Applicant: Mithra Pharmaceuticals S.A., Liège (BE)

(72) Inventor: Séverine Jaspart, Bois-et-Borsu (BE)

(73) Assignee: NOVALON S.A., Liege (BE)

( * ) Notice: Subject to any disclaimer, the term of this patent is extended or adjusted under 35 U.S.C. 154(b) by 0 days.

(21) Appl. No.: 16/095,917

(22) PCT Filed: May 4, 2017

(86) PCT No.: PCT/EP2017/060676
§ 371 (c)(1),
(2) Date: Oct. 23, 2018

(87) PCT Pub. No.: WO2017/191266
PCT Pub. Date: Nov. 9, 2017

(65) Prior Publication Data
US 2019/0134058 A1 May 9, 2019

(30) Foreign Application Priority Data
May 4, 2016 (EP) .................................... 16168390

(51) Int. Cl.
*A61K 31/56* (2006.01)
*A61K 9/20* (2006.01)
*A61K 31/567* (2006.01)

(52) U.S. Cl.
CPC ............ *A61K 31/56* (2013.01); *A61K 9/2018* (2013.01); *A61K 31/567* (2013.01); *A61K 9/2059* (2013.01)

(58) Field of Classification Search
CPC .... A61K 31/56; A61K 31/567; A61K 9/2018; A61K 9/2059
See application file for complete search history.

(56) References Cited

U.S. PATENT DOCUMENTS 4,701,450 A * 10/1987 Kelder ................ A61K 31/565
514/177
2005/0176679 A1   8/2005 Glaenzer

FOREIGN PATENT DOCUMENTS

| CN | 102085193 | * | 6/2011 |
| CN | 102085193 A | | 6/2011 |
| WO | WO 2005/117899 A1 | | 12/2005 |

OTHER PUBLICATIONS

Search Report in International Application No. PCT/EP2017/060676, dated Jul. 5, 2017.

* cited by examiner

*Primary Examiner* — Barbara P Badio
(74) *Attorney, Agent, or Firm* — Knobbe, Martens, Olson & Bear LLP

(57) ABSTRACT

A method of stabilizing tibolone in a solid dosage form using a sugar-alcohol, and a pharmaceutical composition, in particular a solid dosage form such as a tablet, including tibolone, a sugar-alcohol and a non-sugar-alcohol diluent. The weight ratio of the sugar-alcohol to the non-sugar-alcohol diluent is between 4:1 and 1:4.

19 Claims, No Drawings

USE OF SUGAR-ALCOHOLS IN TIBOLONE COMPOSITIONS

RELATED APPLICATIONS

This application is the U.S. National Phase under 35 U.S.C. § 371 of International Application PCT/EP2017/060676, filed May 4, 2017, designating the U.S., and published in English as WO 2017/191266 on Nov. 9, 2017, which claims priority to European Patent Application No. 16168390.9, filed May 4, 2016, the entire contents of which are incorporated herein by reference.

FIELD OF THE INVENTION

The present invention relates to medicinal formulations, in particular formulations of tibolone, more in particular solid dosage forms of tibolone, and to methods for preparing the same.

BACKGROUND OF THE INVENTION

Tibolone ($C_{21}H_{28}O_2$; (7α,17α)-17-hydroxy-7-methyl-19-nor-17-pregn-5(10)-en-20-yn-3-one) is a synthetic steroid with oestrogenic, progestonic and weak androgenic properties. It is used for the treatment of oestrogen deficiency symptoms in postmenopausal women, more than one year after menopause and for prevention of osteoporosis in postmenopausal women at high risk of future fractures who are intolerant of, or contraindicated for, other medicinal products approved for the prevention of osteoporosis.

A typical known formulation of tibolone is a 100 mg tablet comprising 2.5 mg of tibolone, a relatively small amount (e.g. about 1% by weight) of pharmaceutically acceptable auxiliaries such as an antioxidant and/or a lubricant, and a carrier making up the body of the tablet. The carrier is typically composed of about 10% by weight of starch, e.g. potato starch, and about 90% by weight of lactose.

Tibolone, when formulated as a solid dosage form, in particular a tablet, is however relatively unstable. The inherent stability is at least partly due to the presence of degradation products, in particular 10,17-dihydroxy-7α-methyl-19-nor-10ξ,17α-pregn-4-en-20-yn-3-one (impurity A), 10-hydroperoxy-17-hydroxy-7α-methyl-19-nor-10ξ,17α-pregn-4-en-20-yn-3-one (impurity B), and 17-hydroxy-7α-methyl-19-nor-10ξ,17α-pregn-4-en-20-yn-3-one (impurity C), which increase during production of the tablets and during storage. Impurity C is the most difficult to control.

Various attempts have been reported to improve tibolone stability in tablets. EP 0389035 describes a manufacturing process for tibolone tablets which ensures the stability of tibolone. The obtained tablets are available on the market under the name of Livial®. The process encompasses placebo granulation followed by mixing with tibolone, but is complicated and quite expensive. WO 98/47517 pretends to obtain better stability when using a high (more than 10% by weight) percentage of a starch in the tibolone formulation. WO 03/032924 teaches that the inclusion of a pH-adjusting agent increases the stability of tibolone formulations. WO 2005/117899 describes the use of water-soluble starch products, in particular cyclodextrin, as carriers for enhancing storage stability of tibolone formulations. WO 2004/045587 addresses the problem of the tibolone instability by providing the tibolone tablets with a coating. WO 2009/012733 is directed to a manufacturing process for tibolone tablets by direct compression, characterized in that the formulation is exposed to the action of a protic solvent during the process, resulting in more stable tablets.

WO2017047586A1 for example discloses a drug formulation comprising a combination of starch as a desintegrant and mannitol as a diluent.

The present invention aims to provide a tibolone formulation with improved stability, which can be obtained by a simple manufacturing process.

SUMMARY OF THE INVENTION

The present inventors have found that the use of a polyol, optionally in mixture with a non-polyol or non-sugar-alcohol diluent, as diluent in solid dosage forms of tibolone has a stabilizing effect on tibolone. The solid dosage forms not only provide improved tibolone stability, but they can also be obtained by simple manufacturing processes.

The invention therefore provides the following aspects:

Aspect 1: use of a polyol, such as a sugar-alcohol for (chemically) stabilizing tibolone in a solid dosage form. In a preferred embodiment, said stabilizing encompasses reducing the presence of impurities of tibolone, more particularly of impurities A, B and C of tibolone, more preferably impurity C of tibolone. Said impurities are defined in accordance with the European Pharmacopoeia:

| List of Impurities: | Chemical Names |
|---|---|
| Impurity A | 10,17-dihydroxy-7α-methyl-19-nor-10ξ,17α-pregn-4-en-20-yn-3-one, |
| Impurity B | 10-hydroperoxy-17-hydroxy-7α-methyl-19-nor-10ξ,17α-pregn-4-en-20-yn-3-one, |
| Impurity C | 17-hydroxy-7α-methyl-19-nor-10ξ,17α-pregn-4-en-20-yn-3-one, |

The term "stabilizing tibolone" as used herein intends to avoid that the active ingredient (i.e. tibolone) is altered or degraded due to external influences in such a way that it can no longer comply with the desired action in the composition containing them, or can no longer do so to a sufficient extent, or that the altered or degraded products or impurities even display a harmful action. The term hence intends to cover the chemical stabilization or preservation of the active ingredient and not the physical "stabilization" thereof into e.g. a certain dosage form or formulation, having no influence n the polymeric form of the active ingredient. Aspect 2: use according to aspect 1, wherein the polyol is present in the solid dosage form at a concentration of at least 10% by weight.

Aspect 3: use according to any one of aspects 1 or 2, wherein the polyol is a sugar-alcohol selected from the group consisting of: mannitol, maltitol, sorbitol, xylitol, lactitol, and isomalt, or any mixture thereof.

Aspect 4: use according to any one of aspects 1 to 3, wherein the solid dosage form further comprises a non-polyol (non-sugar-alcohol) diluent, and wherein the weight ratio of the polyol or sugar-alcohol to the non-polyol (non-sugar-alcohol) diluent is comprised between 4:1 and 1:4, preferably between 3:1 and 1:3, more preferably between 2:1 and 1:2, most preferably 1:1.

Aspect 5: use according to aspect 4, wherein the non-polyol diluent is a non-sugar-alcohol diluent, more preferably selected from the group consisting of: lactose and lactose monohydrate.

Aspect 6: use according to any one of aspects 1 to 5, wherein the tibolone is present in the solid dosage form at a concentration of between about 0.1 and about 10% by weight, preferably of between about 1 and about 5% by weight, most preferably between about about 1.25 and about 2.5% by weight.

Aspect 7: a pharmaceutical composition in a solid dosage form, comprising tibolone and a mixture of a polyol such as a sugar-alcohol and a non-polyol diluent such as a non-sugar-alcohol diluent, wherein the weight ratio of said polyol to said non-polyol or non-sugar-alcohol diluent is comprised between 4:1 and 1:4, preferably between 3:1 and 1:3, more preferably between 2:1 and 1:2, most preferably 1:1.

Aspect 8: the pharmaceutical composition according to aspect 7, wherein the polyol is a sugar-alcohol selected from the group consisting of: mannitol, maltitol, sorbitol, xylitol, lactitol, and isomalt, or any mixture thereof.

Aspect 9: the pharmaceutical composition according to aspect 7 or 8, wherein the non-polyol diluent is a non-sugar-alcohol diluent, preferably selected from the group consisting of: lactose and lactose monohydrate.

Aspect 10: the pharmaceutical composition according to any one of aspects 7 to 9, comprising tibolone and a mixture of mannitol and lactose, wherein the weight ratio of said mannitol to said lactose is comprised between 4:1 and 1:4, preferably between 3:1 and 1:3, more preferably between 2:1 and 1:2, most preferably 1:1.

Aspect 11: the pharmaceutical composition according to any one of aspects 7 to 10, wherein the tibolone is present at a concentration of between about 0.1 and about 10% by weight, preferably of between about 1 and about 5% by weight, most preferably between about 1.25 and about 2.5% by weight.

Aspect 12: the pharmaceutical composition according to any one of aspects 7 to 11, further comprising a starch at a concentration of 10% by weight or less.

Aspect 13: the pharmaceutical composition according to any one of aspects 7 to 12, further comprising an antioxidant at a concentration comprised between about 0.1 and about 1% by weight.

Aspect 14: the pharmaceutical composition according to any one of aspects 7 to 13, wherein the composition is in the form of a tablet.

Aspect 15: the pharmaceutical composition according to any one of aspects 7 to 14, comprising:
  tibolone at a concentration comprised between about 0.1 and about 10% by weight, preferably between about 1 and about 5% by weight, most preferably between about 1.25 and about 2.5% by weight of the pharmaceutical composition;
  a mixture of mannitol and lactose, wherein the weight ratio of the mannitol to the lactose is comprised between 4:1 and 1:4, preferably between 3:1 and 1:3, more preferably between 2:1 and 1:2, most preferably 1:1, and wherein the mixture constitutes at least 80% by weight of the pharmaceutical composition;
  optionally a starch, preferably potato starch, at a concentration of 10% by weight or less;
  optionally an antioxidant, preferably ascorbyl palmitate, at a concentration comprised between about 0.1 and about 1% by weight, preferably about 0.2% by weight of the pharmaceutical composition;
  optionally a lubricant, preferably magnesium stearate, at a concentration comprised between about 0.1 and about 5% by weight, preferably about 0.5% by weight or about 1% by weight of the pharmaceutical composition.

Aspect 16: a method for preparing a solid dosage form comprising tibolone comprising the following steps:
  a) mixing tibolone with a polyol such as a sugar-alcohol, a non-polyol diluent such as a non-sugar-alcohol diluent, and optionally further excipients, wherein the weight ratio of the polyol to the non-polyol or non-sugar-alcohol diluent is comprised between 4:1 and 1:4, preferably between 3:1 and 1:3, more preferably between 2:1 and 1:2, most preferably 1:1; and
  b) formulating the mixture obtained in step a) into a solid dosage form.

Aspect 17: the method according to aspect 16, wherein said formulation comprises a direct compression procedure, a wet granulation procedure or a dry granulation procedure.

Aspect 18: the method according to aspect 16 or 17, wherein the polyol is a sugar-alcohol selected from the group consisting of: mannitol, maltitol, sorbitol, xylitol, lactitol, and isomalt or any mixture thereof.

Aspect 19: the method according to any one of aspects 16 to 18, wherein the non-polyol diluent is a non-sugar-alcohol diluent, preferably selected from the group consisting of: lactose and lactose monohydrate.

Aspect 20: The method according to any one of aspects 16 to 19, wherein said composition comprises tibolone and a mixture of mannitol and lactose, wherein the weight ratio of said mannitol to said lactose is comprised between 4:1 and 1:4, preferably between 3:1 and 1:3, more preferably between 2:1 and 1:2, most preferably 1:1.

Aspect 21: the method according to any one of aspects 16 to 20, wherein the tibolone in said composition is present at a concentration of between about 0.1 and about 10% by weight, preferably of between about 1 and about 5% by weight, most preferably between about 1.25 and about 2.5% by weight.

Aspect 22: the method according to any one of aspects 16 to 21, wherein said composition further comprises a starch at a concentration of about 10% by weight or less.

Aspect 23: the method according to any one of aspects 16 to 22, wherein said composition further comprises an antioxidant at a concentration comprised between about 0.1 and about 1% by weight.

Aspect 24: the method according to any one of aspects 16 to 23, wherein the composition is made in the form of a tablet.

Aspect 25: the method according to any one of aspects 16 to 24, wherein said composition comprises:
  tibolone at a concentration comprised between about 0.1 and about 10% by weight, preferably of between about 1 and about 5% by weight, most preferably between about 1.25 and 2.5% by weight of the pharmaceutical composition;
  a mixture of mannitol and lactose, wherein the weight ratio of the mannitol to the lactose is comprised between 4:1 and 1:4, preferably between 3:1 and 1:3, more preferably between 2:1 and 1:2, most preferably 1:1, and wherein the mixture constitutes at least 80% by weight of the pharmaceutical composition;
  optionally a starch, preferably potato starch, at a concentration of about 10% by weight or less;
  optionally an antioxidant, preferably ascorbyl palmitate, at a concentration comprised between about 0.1 and about 1% by weight, preferably about 0.2% by weight of the pharmaceutical composition;
  optionally a lubricant, preferably magnesium stearate, at a concentration comprised between about 0.1 and about 5% by weight, preferably about 0.5% by weight or about 1% by weight of the pharmaceutical composition.

DETAILED DESCRIPTION OF INVENTION

Before the present invention is described, it is to be understood that this invention is not limited to particular methods, components, or products described, as such methods, components, and products may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Throughout the present application, components, such as diluents, binding agents, disintegrants, stabilizers, and lubricants, are considered while bearing in mind that some substances may have multiple functions.

The following detailed description is not to be taken in a limiting sense. The scope of the present invention is defined by the appended claims.

The present inventors have found that using a mixture of a sugar-alcohol and a non-sugar-alcohol diluent such as a mixture of mannitol and lactose for formulating tablets of tibolone instead of lactose alone has a stabilizing effect on tibolone in that it avoids the formulation of impurities of tibolone during the shelf-life of the formulation. The tablets of the invention not only provide improved tibolone stability, but they can also be obtained by a simple manufacturing process such as direct compression.

Accordingly, in an aspect the invention is directed to the use of a polyol for stabilizing tibolone in a solid dosage form.

The term "impurities of tibolone" as used herein encompasses all degradation products of tibolone during storage and shelf-life, more particularly the impurities: 10,17-dihydroxy-7α-methyl-19-nor-10ξ,17α-pregn-4-en-20-yn-3-one (impurity A), 10-hydroxyperoxy-17-hydroxy-7α-methyl-19-nor-10ξ,17α-pregn-4-en-20-yn-3-one (impurity B), and/or 17-hydroxy-7α-methyl-19-nor-10ξ,17α-pregn-4-en-20-yn-3-one (impurity C), which increase during production of the tablets and during storage.

As used herein "stabilizing tibolone" refers to keeping impurity levels and/or levels of degradation products of tibolone during the manufacturing process and shelf-life as low as possible. More particularly, it is desired that impurity C levels in tibolone formulations are lower than 3% relative to the tibolone content just after manufacturing, and that they are kept below 4% relative to the tibolone content during shelf-life, of e.g. at least 6 months, preferably at least 12 months, or 18 months. It is further desired that impurity A and B levels in tibolone formulations are limited to maximum 1% relative to the tibolone content each upon manufacturing and at the end of shelf-life, of e.g. at least 6 months, preferably at least 12 months, or 18 months. It has been found that polyols, more particularly sugar-alcohols, preferably mannitol, keep the level of in particular impurity C (i.e. 17-hydroxy-7α-methyl-19-nor-10ξ,17α-pregn-4-en-20-yn-3-one or isotibolone) lower as compared to tibolone formulations without a polyol such as a sugar alcohol. Impurity C levels can be measured according to the provisions of the European Pharmacopoeia currently in force (Monograph 1739). The term "stabilization of tibolone" or "for stabilizing tibolone" should be given its normal meaning in the art of pharmaceutical or medicinal preparations. This implies that the mere effect of adding an excipient or diluent (e.g. a filler) to a pharmaceutical composition in order to e.g. physically form a tablet or other dosage form does not fall under the definition of stabilization of the active ingredient tibolone as used herein. The actual stabilizers of active ingredients are only a subcategory of these diluents or excipients. Excipients such as fillers/diluents used to simply give a dosage form a certain shape are not to be seen as falling within the scope of stabilizers used to stabilize a drug or active substance such as tibolone.

By using a polyol, more particularly a sugar-alcohol, preferably mannitol, for formulating solid dosage units of tibolone, acceptable impurity levels, in particular impurity C levels, below 2%, preferably below 1% such as below 0.9%, below 0.8%, below 0.7%, below 0.6%, below 0.5%, below 0.4%, below 0.3%, below 0.2% or below 0.2% can be obtained just after the manufacturing process. We note that to our knowledge the stabilizing property of sugar-alcohols such as mannitol on active ingredients was not previously known, as is confirmed by the "Handbook of Pharmaceutical Excipients—Seventh Edition—Rowe et al.". This reference book collects essential data on the physical properties of excipients. The functionalities of mannitol as excipient are listed as follows: diluent, plasticizer, sweetening agent, tablet and capsule diluent, tonicity agent. The stabilization effect on the active ingredient was hence clearly not inherently known for sugar-alcohols such as mannitol. It was hence unexpected that replacing a part of the known polyol (or sugar-alcohol) diluent with a non-polyol (or non-sugar-alcohol) diluent could improve the stability of the active ingredient by reducing the breakdown thereof. Especially for tibolone, this resulted in a reduced breakdown of the active ingredient into unwanted impurities.

By using a polyol, more particularly a sugar-alcohol, preferably mannitol, for formulating solid dosage units of tibolone, acceptable impurity levels, in particular impurity C levels, below 3% or below 2% (relative to the tibolone content), preferably below 1% such as below 0.9%, below 0.8%, below 0.7%, below 0.6%, or below 0.5% can be obtained up to 6, 9 or 12 months of storage, preferably up to 24 months, more preferably up to 36 months or longer at a temperature of 25° C. and relative humidity 60±5%.

The formulations or pharmaceutical compositions of tibolone as described herein are preferably solid dosage forms. Non-limiting examples of solid dosage forms include capsules, caplets, gelcaps, cachets, suppositories, pills, pellets, implants, and tablets. In preferred embodiments, the solid dosage form is a tablet.

The solid dosage forms intended herein comprise tibolone or (7α,17α)-17-hydroxy-7-methyl-19-nor-17-pregn-5(10)-en-20-yn-3-one) as active pharmaceutical ingredient (API). Tibolone is known from e.g. U.S. Pat. No. 3,340,279. The amount of tibolone present in the solid dosage forms is preferably comprised between about 0.1 and about 10% by weight, more preferably between about 1 and about 10% by weight, even more preferably between about 1 and about 5% by weight, yet more preferably between about 1.25 and about 2.5% by weight. In certain embodiments, tibolone is present in the solid dosage form at a concentration of about 1.25% by weight or about 2.5% by weight.

Besides the tibolone active ingredient, the solid dosage forms intended herein further comprise a pharmaceutically acceptable carrier, which makes up the body of the solid dosage form. The solid dosage forms described herein are characterized in that the carrier comprises at least a polyol.

It is to be understood that the present invention is not limited to the use of a single type of polyol or sugar-alcohol, in the solid dosage forms described herein, but also mixtures of two or more types of polyols or sugar-alcohols are comprised within the term "a polyol" as used herein and are intended herein.

The term "polyol" or "polyalcohol" refers to an alcohol comprising multiple hydroxyl groups such as a sugar alcohol (i.e. an alcohol prepared from sugar). Preferably, the polyol in the solid dosage forms described herein is a sugar-alcohol. In embodiments, the polyol is selected from the group consisting of mannitol, maltitol, sorbitol, xylitol, lactitol, isomalt and any mixture thereof, preferably mannitol.

In embodiments, the polyol is present in the solid dosage form at a concentration of at least 10% by weight, preferably at least about 20% by weight, more preferably at least about 40% by weight.

"Diluents" or "fillers" or "filling excipients" usually make up the major portion of the carrier. Non-limiting examples of suitable diluents for solid dosage forms include sugars such as lactose (including lactose monohydrate and anhydrous lactose), celluloses and/or cellulose derivatives (e.g. microcrystalline cellulose), starches such as corn, potato, rice or wheat starch, inorganic fillers such as calcium hydrogen phosphate, polyalcohols such as sorbitol or mannitol, and organic calcium salts such as calcium lactate.

The present inventors have found that a solid dosage form of tibolone with improved stability (reduced formation of tibolone impurities during the shelf-life) can be obtained by using a polyol, more particularly a sugar-alcohol. The polyol such as sugar-alcohol can be the sole component in the solid dosage form, or it can be present in a mixture with one or more further, non-polyol or non-sugar-alcohol diluents. Indeed, the present inventors have surprisingly found that when using a mixture of a polyol or sugar-alcohol and a further, non-polyol or non-sugar-alcohol diluent for the formulation of a solid dosage form of tibolone instead of said non-polyol or non-sugar-alcohol diluent alone, the stability of the solid dosage form is improved. The weight ratio of the polyol or sugar-alcohol to the non-polyol or non-sugar-alcohol diluent in said mixture is preferably comprised between 5:1 to 1:5, more preferably between 4:1 and 1:4, even more preferably between 2:1 and 1:2, most preferably about 1:1. Said non-polyol or non-sugar-alcohol diluent in the mixture is preferably lactose monohydrate or anhydrous lactose.

Consequently, in an aspect the invention provides a (pharmaceutical) composition or formulation comprising tibolone and a mixture of a polyol or sugar-alcohol and a non-polyol or non-sugar-alcohol diluent, wherein the weight ratio of said polyol or sugar-alcohol to said non-polyol or non-sugar-alcohol diluent is comprised between 4:1 and 1:4, preferably between 2:1 and 1:2, more preferably about 1:1.

Optionally, the carrier may further comprise a binding agent. "Binding agents" or "binders" provide cohesiveness to the formulation or pharmaceutical composition. The binder may in principle be any suitable pharmaceutical binder such as starches (such as corn starch, potato starch, wheat starch, or dextrins such as maltodextrins), celluloses and cellulose derivatives (e.g., carboxymethylcellulose, hydroxypropylcellulose, hydroxypropylmethylcellulose, or methylcellulose) or polymers (such as polyvinyl pyrrolidone).

In preferred embodiments, the solid dosage form further comprises a starch, such as potato starch. In embodiments, a starch, in particular potato starch, is present in the solid dosage forms described herein at a concentration of about 10% by weight or less. Starches are also known for their capacity as "disintegrants", i.e. a component integrated into a solid dosage form to help it break up and dissolve to release the active component.

In addition to the stabilizing effect provided by the polyol or sugar-alcohol, other "stabilizers" or "stabilizing agents" may be included in the solid dosage forms described herein. Non-limiting examples of such stabilizing agents are anti-oxidants (such as e.g. ascorbyl palmitate, ascorbyl stearate, ascorbic acid, alpha-tocopherol, butylated hydroxyanisole, and butylhydroxytoluene) and chelating agents (such as e.g. sodium EDTA and sodium ascorbate). In certain embodiments, the solid dosage form further comprises an antioxidant, such as ascorbyl palmitate. The antioxidant may be present in the solid dosage form at a concentration comprised between about 0.1 and about 1% by weight, preferably about 0.2% by weight.

In addition, the solid dosage form may include components which help to impart satisfactory processing characteristics to the formulation such as lubricants. "Lubricants" prevent friction and wear during processing. For example, stearate-type lubricants such as magnesium stearate; talcum;

stearic acid; sodium stearyl fumarate; hydrogenated vegetable oil; or high melting point waxes, preferably magnesium stearate, may be present in the solid dosage forms described herein. Lubricants may be present in the solid dosage forms described herein at a concentration comprised between about 0.1 and about 5% by weight, preferably between about 0.5 and about 1% by weight.

A preferred pharmaceutical composition or formulation, in particular a solid dosage form, more particularly a tablet, of the invention comprises:
  tibolone at a concentration comprised between about 0.1 and about 10% by weight, preferably between about 1 and about 5% by weight, more preferably between about 1.25 and about 2.5% by weight;
  a mixture of mannitol and lactose, wherein the weight ratio of the mannitol to the lactose is 1:1, at a concentration of at least about 80% by weight;
  a starch, preferably potato starch, at a concentration of about 10% by weight or less;
  optionally an antioxidant, preferably ascorbyl palmitate, at a concentration comprised between about 0.1 and about 1% by weight, preferably about 0.2% by weight;
  a lubricant, preferably magnesium stearate, at a concentration comprised between about 0.1 and about 5% by weight, preferably about 0.5% by weight or about 1% by weight.

Advantageously, the solid dosage forms described herein can be obtained by simple manufacturing processes such as e.g. direct compression, wet-granulation, and dry-granulation. The methods for manufacturing a solid dosage form as described herein are characterized in that they comprise a mixing step of mixing tibolone with a polyol or sugar-alcohol, a non-polyol or non-sugar-alcohol diluent, and optionally further components, wherein the weight ratio of the polyol to the non-polyol or non-sugar-alcohol diluent is comprised between 4:1 and 1:4, preferably between 3:1 and 1:3, more preferably between 2:1 and 1:2, most preferably 1:1.

Accordingly, the present invention also pertains to a method for preparing a solid dosage form comprising tibolone as described herein comprising the following steps:
  a) mixing tibolone with a polyol or sugar-alcohol and a non-polyol or non-sugar-alcohol diluent and the further components (if any), wherein the weight ratio of the polyol or sugar-alcohol to the non-polyol or non-sugar-alcohol diluent is comprised between 4:1 and 1:4, preferably between 3:1 and 1:3, more preferably between 2:1 and 1:2, most preferably 1:1 and
  b) formulating the mixture obtained in step a) to form a solid dosage form.

In embodiments, said formulation step comprises a direct compression procedure, a wet granulation procedure or a dry granulation procedure.

A direct compression process typically involves weighing the components, mixing of the components, lubrication and compressing the resulting mixture so as to form a solid dosage form, in particular a tablet.

Accordingly, the present invention also pertains to a method for preparing a solid dosage form comprising tibolone as described herein comprising the following steps:
  a) mixing tibolone with a polyol or sugar-alcohol and a non-polyol or non-sugar-alcohol diluent and the further components (if any), wherein the weight ratio of the polyol or sugar-alcohol to the non-polyol or non-sugar-alcohol diluent is comprised between 4:1 and 1:4, preferably between 3:1 and 1:3, more preferably between 2:1 and 1:2, most preferably 1:1 and
  b) compressing the mixture obtained in step a) to form a solid dosage form.

Wet-granulation involves weighing the components, including a solvent, mixing of the components, granulating them, drying them, lubrication, and compressing the resultant admixture into a solid dosage form.

Dry-granulation is distinguished from wet granulation in that no solvent is applied to produce the granules.

Also disclosed herein is a solid dosage form, in particular a tablet, of tibolone obtained by a method as described herein.

EXAMPLES

Example 1: Evaluation of Mannitol in Solid Dosage Forms Comprising Tibolone

Tibolone tablets were manufactured by a conventional direct compression process. The composition of the tablets is summarized in Table 2. Briefly, the raw materials were weighed, sieved and homogenized. Following homogenization, the mixture was compressed into tablets. Just after production (i.e. at t=0), the tablets were analyzed for tibolone impurities by a chromatography (HPLC) method that allows a suitable separation between the peaks of impurities A, B and C (Tibolone degradation products described in the current European Pharmacopeia Monograph 1739) under the following conditions:
  Equipment: HPLC system
  Pre-column: Universal RP, EC 4/3
  Stationary phase: Nucleodur 100-3 C18ec Particulars' diameter: 3 μm
  Length: 150 mm
  Internal diameter: 4.6 mm
  Mobile phase:
    Solvent A: water for chromatography R
    Solvent B: Acetonitrile for chromatography R
  Gradient program:

TABLE 1

Gradient program of the mobile phase of the HPLC method.

| Time (min) | Solvent A (%) | Solvent B (%) |
|---|---|---|
| 0 | 65 | 35 |
| 10 | 50 | 50 |
| 30 | 50 | 50 |
| 35 | 65 | 35 |
| 40 | 65 | 35 |

Flow: 1.5 ml/min
Wavelength: 210 nm
Injection volume: 20 μl
Column temperature: 40° C.
Run time: 40 min

TABLE 2

Composition of the tibolone tablets. Quantity of the components is indicated in mg per tablet.

| | | batch | | |
|---|---|---|---|---|
| Component | Function | Batch #1 | Batches #2, #3 and #4 | Batch #5 |
| tibolone | API | 2.5 | 2.5 | 2.5 |
| lactose monohydrate | diluent | 86.3 | 43.15 | 43.4 |
| mannitol | diluent | — | 43.15 | 43.4 |

TABLE 2-continued

Composition of the tibolone tablets. Quantity of the components is indicated in mg per tablet.

| Component | Function | Batch #1 | Batches #2, #3 and #4 | Batch #5 |
|---|---|---|---|---|
| potato starch | binder/disintegrant | 10 | 10 | 10 |
| ascorbyl palmitate | antioxidant | 0.2 | 0.2 | 0.2 |
| magnesium stearate | lubricant | 1 | 1 | 0.5 |

The tablets were packed into PVC/Aluminium blisters and stored either 1) at a temperature of 25° C. and a relative humidity of 60% (long term stability conditions for Zone II), 2) at a temperature of 40° C. and a relative humidity of 75% (accelerated stability conditions), or 3) at ambient conditions (laboratory conditions, less than 25° C., no humidity control). After 1, 2, 3 and/or 6 months of storage (up to 18 months for batches #2 and #3), the tablets were analyzed for tibolone impurities. The impurity levels of the different tablet batches are summarized in Tables 3 to 6.

TABLE 3

Impurity C levels (in % relative to tibolone content) in the tested tablets.

| | | without mannitol Batch #1 | with mannitol Batch #2 | Batch #3 | Batch #4 | Batch #5 |
|---|---|---|---|---|---|---|
| 25° C./60% RH | t = 0 | 0.66 | 0.33 | 0.31 | 0.42 | 0.6 |
| | t = 1 month | 1.6 | ND | ND | ND | 0.65 |
| | t = 2 months | 1.63 | ND | ND | ND | ND |
| | t = 3 months | 1.93 | 0.47 | 0.48 | 0.74 | 0.71 |
| | t = 6 months | 1.44 | 0.67 | 0.89 | 0.80 | 0.89 |
| | T = 9 months | — | 0.75 | 0.72 | 0.85 | — |
| | T = 12 months | — | 0.81 | 0.83 | 0.78 | — |
| | T = 18 months | — | 1.01 | 1.05 | 1.05 | — |
| | T = 24 months | — | 0.94 | 0.97 | In progress | — |
| 40° C./75% RH | t = 1 month | 1.88 | ND | ND | ND | 0.82 |
| | t = 2 months | 2.02 | ND | ND | ND | ND |
| | t = 3 months | 2.39 | 1.11 | 1.14 | 1.66 | 1.02 |
| | t = 6 months | 1.89 | 1.74 | 1.82 | 2.10 | 1.61 |
| Ambient conditions | t = 3 months | 1.99 | ND | ND | ND | 0.7 |

ND = not determined

TABLE 4

Impurity A levels (in % relative to tibolone content) in the tested tablets.

| | | without mannitol Batch #1 | with mannitol Batch #2 | Batch #3 | Batch #4 | Batch #5 |
|---|---|---|---|---|---|---|
| 25° C./60% RH | t = 0 | <0.05 | 0.14 | 0.08 | 0.14 | <0.05 |
| | t = 1 month | 0.28 | ND | ND | ND | 0.29 |
| | t = 2 months | 0.46 | ND | ND | ND | ND |
| | t = 3 months | 0.33 | 0.24 | 0.24 | 0.35 | 0.35 |
| | t = 6 months | 0.34 | 0.34 | 0.42 | 0.37 | 0.32 |
| | T = 9 months | — | 0.41 | 0.36 | 0.36 | — |
| | T = 12 months | — | 0.42 | 0.41 | 0.24 | — |
| | T = 18 months | — | 0.50 | 0.51 | 0.46 | — |
| | T = 24 months | — | 0.36 | 0.37 | In progress | — |
| 40° C./75% RH | t = 1 month | 0.39 | ND | ND | ND | 0.39 |
| | t = 2 months | 0.47 | ND | ND | ND | ND |
| | t = 3 months | 0.51 | 0.41 | 0.40 | 0.51 | 0.48 |
| | t = 6 months | 0.53 | 0.58 | 0.60 | 0.55 | 0.48 |
| Ambient conditions | t = 3 months | 0.22 | ND | ND | ND | 0.28 |

ND = not determined

TABLE 5

Impurity B levels (in % relative to tibolone content) in the tested tablets.

| | | without mannitol Batch #1 | with mannitol Batch #2 | Batch #3 | Batch #4 | Batch #5 |
|---|---|---|---|---|---|---|
| 25° C./60% RH | t = 0 | 0.07 | 0.12 | 0.09 | 0.08 | 0.08 |
| | t = 1 month | 0.23 | ND | ND | ND | 0.05 |
| | t = 2 months | 0.25 | ND | ND | ND | ND |
| | t = 3 months | 0.14 | <0.05 | <0.05 | 0.05 | 0.06 |
| | t = 6 months | 0.18 | 0.08 | 0.06 | 0.07 | <0.05 |
| | T = 9 months | — | 0.13 | <0.05 | 0.05 | — |
| | T = 12 months | — | 0.11 | 0.11 | <0.05 | — |
| | T = 18 months | — | 0.15 | 0.18 | 0.18 | — |
| | T = 24 months | — | <0.05 | <0.05 | in progress | — |
| 40° C./75% RH | t = 1 month | 0.24 | ND | ND | ND | 0.05 |
| | t = 2 months | 0.19 | ND | ND | ND | ND |
| | t = 3 months | 0.22 | 0.10 | 0.09 | 0.10 | 0.08 |
| | t = 6 months | 0.32 | 0.29 | 0.30 | 0.23 | 0.10 |
| Ambient conditions | t = 3 months | 0.14 | ND | ND | ND | 0.16 |

ND = not determined

TABLE 6

Total impurities, except C, levels (in % relative to tibolone content) in the tested tablets.

|  |  | without mannitol Batch #1 | with mannitol | | | |
|---|---|---|---|---|---|---|
|  |  |  | Batch #2 | Batch #3 | Batch #4 | Batch #5 |
| 25° C./60% RH | t = 0 | 0.07 | 0.26 | 0.17 | 0.22 | 0.16 |
|  | t = 1 month | 0.79 | ND | ND | ND | 0.29 |
|  | t = 2 months | 0.71 | ND | ND | ND | ND |
|  | t = 3 months | 0.59 | 0.24 | 0.24 | 0.40 | 0.51 |
|  | t = 6 months | 1.3 | 0.42 | 0.49 | 0.65 | 0.32 |
|  | T = 9 months | — | 0.84 | 0.36 | 0.80 | — |
|  | T = 12 months | — | 0.60 | 0.64 | 0.24 | — |
|  | T = 18 months | — | 0.85 | 0.95 | 1.71 | — |
|  | T = 24 months | — | 0.36 | 0.37 | in progress | — |
| 40° C./75% RH | t = 1 month | 1.19 | ND | ND | ND | 0.39 |
|  | t = 2 months | 0.73 | ND | ND | ND | ND |
|  | t = 3 months | 1.03 | 0.51 | 0.50 | 0.67 | 0.70 |
|  | t = 6 months | 1.9 | 1.03 | 1.06 | 1.07 | 0.65 |
| Ambient conditions | t = 3 months | 0.48 | ND | ND | ND | 0.49 |

ND = not determined

Table 2 shows that the level of impurity C is lower just after production (i.e. at t=0) when a mixture of lactose and mannitol is used instead of lactose only. During stability studies, the increase of impurity C and of total impurities levels is less pronounced for the tablets containing mannitol. The level of impurity C and of total impurities is less after 24 months at 25° 0160% RH for batches with mannitol compared with t=6 months for batch without mannitol (see Table 3); No significant differences have been observed between formulations with or without mannitol for the impurity A and B levels.

Example 2: Evaluation of EDTA

Tibolone tablets as indicated in Table 7 were manufactured, stored and analyzed as described in Example 1.

TABLE 7

Composition of the tibolone tablets. Quantity of the components is indicated in mg per tablet.

| | | batch | | | |
|---|---|---|---|---|---|
| Component | Function | Batch #1 | Batch #6 and Batch #7 | Batch #8 and Batch #9 | Batch #5 |
| tibolone | API | 2.5 | 2.5 | 2.5 | 2.5 |
| lactose monohydrate | diluent | 86.3 | 86.7 | 43.35 | 43.4 |
| mannitol | diluent | — | — | 43.35 | 43.4 |
| EDTA |  | — | 0.1 | 0.1 | — |
| potato starch | binder/disintegrant | 10 | 10 | 10 | 10 |
| ascorbyl palmitate | antioxidant | 0.2 | 0.2 | 0.2 | 0.2 |
| magnesium stearate | lubricant | 1 | 0.5 | 0.5 | 0.5 |

TABLE 8

Impurity C levels (in % relative to tibolone content) in the tested tablets.

|  |  | without mannitol | | | with mannitol | | |
|---|---|---|---|---|---|---|---|
|  |  | without EDTA | with EDTA | | with EDTA | | without EDTA |
|  |  | Batch #1 | Batch #6 | Batch #7 | Batch #8 | Batch #9 | Batch #5 |
| 25° C./60% RH | t = 0 | 0.66 | 2.03 | 0.99 | 0.53 | 0.4 | 0.6 |
|  | t = 1 month | 1.6 | 2.12 | 2.58 | 0.68 | 0.49 | 0.65 |
|  | t = 2 months | 1.63 | 2.21 | 2.64 | 0.8 | ND | ND |
|  | t = 3 months | 1.93 | ND | ND | 0.89 | 0.56 | 0.71 |
|  | t = 6 months | 1.44 | ND | ND | 0.87 | 0.70 | 0.89 |
|  | t = 9 months | — | — | — | — | 0.65 | — |
|  | t = 12 months | — | — | — | — | 0.93 | — |
|  | t = 18 months | — | — | — | — | 1.02 | — |
| 40° C./75% RH | t = 1 month | 1.88 | 2.3 | 2.59 | 0.92 | 0.68 | 0.82 |
|  | t = 2 months | 2.02 | 2.42 | 2.6 | 1.17 | ND | ND |
|  | t = 3 months | 2.39 | ND | ND | 1.4 | 0.91 | 1.02 |

TABLE 8-continued

Impurity C levels (in % relative to tibolone content) in the tested tablets.

| | | without mannitol | | | with mannitol | | without EDTA |
|---|---|---|---|---|---|---|---|
| | | without EDTA | with EDTA | | with EDTA | | |
| | | Batch #1 | Batch #6 | Batch #7 | Batch #8 | Batch #9 | Batch #5 |
| | t = 6 months | 1.89 | ND | ND | 1.66 | 1.44 | 1.61 |
| Ambient conditions | t = 3 months | 1.99 | ND | ND | 0.83 | ND | 0.7 |

ND = not determined

TABLE 9

Impurity A levels (in % relative to tibolone content) in the tested tablets.

| | | without mannitol | | | with mannitol | | without EDTA |
|---|---|---|---|---|---|---|---|
| | | without EDTA | with EDTA | | with EDTA | | |
| | | Batch #1 | Batch #6 | Batch #7 | Batch #8 | Batch #9 | Batch #5 |
| | t = 0 | <0.05 | 0.2 | <0.05 | 0.24 | 0.09 | <0.05 |
| 25° C./ 60% RH | t = 1 month | 0.28 | 0.64 | 0.55 | 0.78 | 0.31 | 0.29 |
| | t = 2 months | 0.46 | 0.42 | 0.39 | 0.57 | ND | ND |
| | t = 3 months | 0.33 | ND | ND | 0.62 | 0.38 | 0.35 |
| | t = 6 months | 0.34 | ND | ND | 0.57 | 0.33 | 0.32 |
| | t = 9 months | — | — | — | — | 0.34 | — |
| | t = 12 months | — | — | — | — | 0.48 | — |
| | t = 18 months | — | — | — | — | 0.48 | — |
| 40° C./ 75% RH | t = 1 month | 0.39 | 0.73 | 0.55 | 0.7 | 0.44 | 0.39 |
| | t = 2 months | 0.47 | 0.45 | 0.37 | 0.65 | ND | ND |
| | t = 3 months | 0.51 | ND | ND | 0.72 | 0.49 | 0.48 |
| | t = 6 months | 0.53 | ND | ND | 0.75 | 0.46 | 0.48 |
| Ambient conditions | t = 3 months | 0.22 | ND | ND | 0.66 | ND | 0.28 |

ND = not determined

TABLE 10

Impurity B levels (in % relative to tibolone content) in the tested tablets.

| | | without mannitol | | | with mannitol | | without EDTA |
|---|---|---|---|---|---|---|---|
| | | without EDTA | with EDTA | | with EDTA | | |
| | | Batch #1 | Batch #6 | Batch #7 | Batch #8 | Batch #9 | Batch #5 |
| | t = 0 | 0.07 | 0.18 | 0.07 | 0.23 | 0.07 | 0.08 |
| 25° C./ 60% RH | t = 1 month | 0.23 | 0.23 | 0.21 | 0.27 | <0.05 | 0.05 |
| | t = 2 months | 0.25 | 0.11 | 0.09 | 0.15 | ND | ND |

TABLE 10-continued

Impurity B levels (in % relative to tibolone content) in the tested tablets.

|  |  | without mannitol | | | with mannitol | | |
|---|---|---|---|---|---|---|---|
|  |  | without EDTA | with EDTA | | with EDTA | | without EDTA |
|  |  | Batch #1 | Batch #6 | Batch #7 | Batch #8 | Batch #9 | Batch #5 |
|  | t = 3 months | 0.14 | ND | ND | 0.16 | 0.07 | 0.06 |
|  | t = 6 months | 0.18 | ND | ND | 0.10 | <0.05 | <0.05 |
|  | t = 9 months | — | — | — | — | 0.09 | — |
|  | t = 12 months | — | — | — | — | 0.12 | — |
|  | t = 18 months | — | — | — | — | 0.12 | — |
| 40° C./ 75% RH | t = 1 month | 0.24 | 0.24 | 0.21 | 0.23 | 0.06 | 0.05 |
|  | t = 2 months | 0.19 | 0.17 | 0.11 | 0.22 | ND | ND |
|  | t = 3 months | 0.22 | ND | ND | 0.24 | 0.1 | 0.08 |
|  | t = 6 months | 0.32 | ND | ND | 0.27 | 0.06 | 0.10 |
| Ambient conditions | t = 3 months | 0.14 | ND | ND | 0.61 | ND | 0.16 |

ND = not determined

TABLE 11

Total impurities, except C, levels (in % relative to tibolone content) in the tested tablets.

|  |  | without mannitol | | | with mannitol | | |
|---|---|---|---|---|---|---|---|
|  |  | without EDTA | with EDTA | | with EDTA | | without EDTA |
|  |  | Batch #1 | Batch #6 | Batch #7 | Batch #8 | Batch #9 | Batch #5 |
|  | t = 0 | 0.07 | 0.5 | 0.07 | 0.54 | 0.25 | 0.16 |
| 25° C./ 60% RH | t = 1 month | 0.79 | 0.87 | 0.76 | 1.06 | 0.31 | 0.29 |
|  | t = 2 months | 0.71 | 0.65 | 0.53 | 0.87 | ND | ND |
|  | t = 3 months | 0.59 | ND | ND | 1.04 | 0.45 | 0.51 |
|  | t = 6 months | 1.3 | ND | ND | 0.81 | 0.33 | 0.32 |
|  | t = 9 months | — | — | — | — | 0.43 | — |
|  | t = 12 months | — | — | — | — | 1.04 | — |
|  | t = 18 months | — | — | — | — | 0.90 | — |
| 40° C./ 75% RH | t = 1 month | 1.19 | 0.97 | 0.75 | 0.99 | 0.49 | 0.39 |
|  | t = 2 months | 0.73 | 0.82 | 0.62 | 1.11 | ND | ND |
|  | t = 3 months | 1.03 | ND | ND | 1.33 | 0.9 | 0.7 |
|  | t = 6 months | 1.9 | ND | ND | 1.17 | 0.59 | 0.65 |
| Ambient conditions | t = 3 months | 0.48 | ND | ND | 1.58 | ND | 0.49 |

ND = not determined

It can be concluded from Tables 8-11 that impurity C level at t=0 (just after production) and during storage is lower when a mixture of lactose and mannitol is used instead of lactose alone. EDTA does not further stabilize the solid dosage form.

Example 3: Evaluation of Ascorbyl Palmitate

Tibolone tablets as indicated in Table 12 were manufactured, stored and analyzed as described in Example 1.

TABLE 12

Composition of the tibolone tablets. Quantity of the components is indicated in mg per tablet.

| Component | Function | batch Batch #5 | Batch #10 |
|---|---|---|---|
| tibolone | API | 2.5 | 2.5 |
| lactose monohydrate | diluent | 43.4 | 43.5 |
| mannitol | diluent | 43.4 | 43.5 |
| potato starch | binder/disintegrant | 10 | 10 |
| ascorbyl palmitate | antioxidant | 0.2 | — |
| magnesium stearate | lubricant | 0.5 | 0.5 |

TABLE 13

Impurity C levels (in % relative to tibolone content) in the tested tablets.

| | | Batch #5 | Batch #10 |
|---|---|---|---|
| | t = 0 | 0.6 | 0.75 |
| 25° C./ | t = 1 month | 0.65 | 0.94 |
| 60% RH | t = 2 months | ND | ND |
| | t = 3 months | 0.71 | 0.98 |
| | t = 6 months | 0.89 | 1.29 |
| 40° C./ | t = 1 month | 0.82 | 1.19 |
| 75% RH | t = 2 months | ND | ND |
| | t = 3 months | 1.02 | 1.39 |
| | t = 6 months | 1.61 | 2.01 |
| Ambient conditions | t = 3 months | 0.7 | 0.94 |

ND = not determined

TABLE 14

Impurity A levels (in % relative to tibolone content) in the tested tablets.

| | | Batch #5 | Batch #10 |
|---|---|---|---|
| | t = 0 | <0.05 | <0.05 |
| 25° C./ | t = 1 month | 0.29 | 0.18 |
| 60% RH | t = 2 months | ND | ND |
| | t = 3 months | 0.35 | 0.25 |
| | t = 6 months | 0.32 | 0.23 |
| 40° C./ | t = 1 month | 0.39 | 0.36 |
| 75% RH | t = 2 months | ND | ND |
| | t = 3 months | 0.48 | 0.45 |
| | t = 6 months | 0.48 | 0.51 |
| Ambient conditions | t = 3 months | 0.28 | 0.18 |

ND = not determined

TABLE 15

Impurity B levels (in % relative to tibolone content) in the tested tablets.

| | | Batch #5 | Batch #10 |
|---|---|---|---|
| | t = 0 | 0.08 | 0.1 |
| 25° C./ | t = 1 month | 0.05 | 0.25 |
| 60% RH | t = 2 months | ND | ND |
| | t = 3 months | 0.06 | 0.28 |
| | t = 6 months | <0.05 | 0.34 |
| 40° C./ | t = 1 month | 0.05 | 0.46 |
| 75% RH | t = 2 months | ND | ND |
| | t = 3 months | 0.08 | 0.66 |
| | t = 6 months | 0.10 | 0.97 |
| Ambient conditions | t = 3 months | 0.16 | 0.48 |

ND = not determined

TABLE 16

Total impurities, except C, levels (in % relative to tibolone content) in the tested tablets.

| | | Batch #5 | Batch #10 |
|---|---|---|---|
| | t = 0 | 0.16 | 0.1 |
| 25° C./ | t = 1 month | 0.29 | 0.44 |
| 60% RH | t = 2 months | ND | ND |
| | t = 3 months | 0.51 | 0.99 |
| | t = 6 months | 0.32 | 0.57 |
| 40° C./ | t = 1 month | 0.39 | 0.95 |
| 75% RH | t = 2 months | ND | ND |
| | t = 3 months | 0.7 | 1.6 |
| | t = 6 months | 0.65 | 1.67 |
| Ambient conditions | t = 3 months | 0.49 | 1 |

ND = not determined

The antioxidant ascorbyl palmitate has an additional stabilizing effect on tibolone in the tablets. It is most likely that ascorbyl palmitate limits the oxidation of impurity C to B and thereby shifts the equilibrium towards a limitation of the emergence of impurity C. It has indeed been observed that the impurity C level is lower in the batch containing ascorbyl palmitate.

Example 4: Evaluation of the Concentration of Mannitol in Solid Dosage Forms Comprising Tibolone Tibolone tablets as indicated in Table 17 are manufactured as described in Example 1. The tablets have been analyzed for tibolone impurities just after manufacture (t=0), and for Impurity C after 2 and 6 months of storage at 25° C. and a relative humidity of 60%.

TABLE 17

Composition of the tibolone tablets. Quantity of the components is indicated in mg per tablet.

| Component | Function | Batch #11 | Batch #12 | Batch #13 | Batch #14 |
|---|---|---|---|---|---|
| | API | 2.5 | 2.5 | 2.5 | 2.5 |
| lactose monohydrate | diluent | 86.3 | 0 | 64.3 | 22 |
| mannitol | diluent | 0 | 86.3 | 22 | 64.3 |
| potato starch | binder/disintegrant | 10 | 10 | 10 | 10 |

TABLE 17-continued

Composition of the tibolone tablets. Quantity of the components is indicated in mg per tablet.

| Component | Function | Batch #11 | Batch #12 | Batch #13 | Batch #14 |
|---|---|---|---|---|---|
| ascorbyl palmitate | antioxidant | 0.2 | 0.2 | 0.2 | 0.2 |
| magnesium stearate | lubricant | 1 | 1 | 1 | 1 |

TABLE 18

Evaluation of impurities data in the tested tablets: Influence of the ratio lactose/mannitol.

| | | Batch #11 | Batch #12 | Batch #13 | Batch #14 |
|---|---|---|---|---|---|
| Impurity A (%) | t = 0 | 0.06 | 0.14 | 0.07 | 0.08 |
| Impurity B (%) | t = 0 | 0.06 | 0.25 | 0.06 | 0.11 |
| Impurity C (%) | t = 0 | 1.35 | 0.31 | 0.46 | 0.32 |
| 25° C./60% RH | t = 2 months | 1.62 | 0.44 | 0.70 | 0.47 |
| | t = 6 months | 1.83 | 0.66 | 0.93 | 0.66 |
| Total impurities (except C) (%) | t = 0 | 0.20 | 0.49 | 0.20 | 0.19 |

From Table 18 it can be concluded that the use of mannitol instead of lactose (partially or totally) limits the emergence of Impurity C. Indeed batch #11 which does not contain mannitol has a significantly higher percentage of impurity C compared to batches containing mannitol, the best results in terms of impurity C being obtained for the batches with a higher ratio of mannitol/lactose. This trend is confirmed by the results obtained after 2 and 6 months at 25° C./60% RH.

Example 5: Evaluation of Different Polyols

Tibolone tablets as indicated in Table 19 are manufactured as described in Example 1. The tablets have been analyzed for tibolone impurities just after manufacture (t=0), and for Impurity C after 2 and 6 months of storage at 25° C. and a relative humidity of 60%. or after 2, 3 and 6 months of storage at 40° C. and a relative humidity of 75%.

TABLE 19

Composition of the tibolone tablets. Quantity of the components is indicated in mg per tablet.

| Component | Function | Batch #15 | Batch #16 | Batch #17 |
|---|---|---|---|---|
| tibolone | API | 2.5 | 2.5 | 2.5 |
| lactose monohydrate | diluent | 43.15 | 43.15 | 43.15 |
| Sorbitol | Diluent-sugar alcohol | 43.15 | — | — |
| Xylitol | Diluent-sugar alcohol | — | 43.15 | — |
| Maltitol | Diluent-sugar alcohol | — | — | 43.15 |
| potato starch | binder/disintegrant | 10 | 10 | 10 |
| ascorbyl palmitate | antioxidant | 0.2 | 0.2 | 0.2 |
| magnesium stearate | lubricant | 1 | 1 | 1 |

TABLE 20

Evaluation of impurities data in the tested tablets using different sugar alcohols as diluents.

| | | Batch #15 | Batch #16 | Batch #17 |
|---|---|---|---|---|
| Impurity A (%) | t = 0 | 0.04 | 0.05 | 0.06 |
| Impurity B (%) | t = 0 | 0.05 | 0.06 | 0.09 |
| Impurity C (%) | t = 0 | 0.55 | 0.36 | 0.38 |
| 25° C./60% RH | t = 2 months | 0.74 | 0.54 | 0.56 |
| | t = 6 months | 0.92 | 0.73 | 0.78 |
| Total impurities (except C) (%) | t = 0 | 0.12 | 0.12 | 0.15 |

From Table 20, it can be concluded that the use of other sugar alcohols like sorbitol, xylitol and maltitol in a mixture with lactose also limits the emergence of Impurity C, compared to the batches using lactose alone in the formulation (batches #2, #3, #4 and #11).

These results show that the stabilizing effect of mannitol when used as diluent in Tibolone tablets can be extended to other sugar alcohols as well.

The invention claimed is:

1. A method of stabilizing tibolone in a solid dosage form, comprising reducing the presence of 17-hydroxy-7α-methyl-19-nor-10ξ,17α-pregn-4-en-20-yn-3-one of said tibolone below 3% relative to the tibolone content, by incorporating lactose and mannitol into said solid dosage form, wherein the weight ratio of the mannitol to the lactose is between 4:1 and 1:2, and wherein a mixture of said mannitol and said lactose is present in the solid dosage form at a concentration of at least 80% by weight, wherein the tibolone is present in the solid dosage form at a concentration of between 1 and 5% by weight.

2. A pharmaceutical composition in a solid dosage form, comprising tibolone and a mixture of a sugar-alcohol and a non-sugar-alcohol diluent, wherein the weight ratio of said sugar-alcohol to said non-sugar-alcohol diluent is comprised between 4:1 and 1:2, wherein the sugar-alcohol is selected from the group consisting of: mannitol, maltitol, sorbitol, xylitol, lactitol, and isomalt, or any mixture thereof, wherein the non-sugar-alcohol diluent is selected from the group consisting of: lactose and lactose monohydrate, wherein a mixture of the sugar alcohol and the non-sugar alcohol is present in the solid dosage form at a concentration of at least 80% by weight, and wherein the tibolone is present in the solid dosage form at a concentration of between 1 and 5% by weight.

3. The pharmaceutical composition according to claim 2, wherein said sugar-alcohol is selected from the group consisting of mannitol, maltitol, and xylitol.

4. The pharmaceutical composition according to claim 2, wherein said mixture comprises mannitol and lactose.

5. The pharmaceutical composition according to claim 2, further comprising a starch at a concentration of 10% by weight or less.

6. The pharmaceutical composition according to claim 2, further comprising an antioxidant at a concentration comprised between 0.1 and 1% by weight.

7. The pharmaceutical composition according to claim 2, wherein the composition is in the form of a tablet.

8. The pharmaceutical composition according to claim 2, comprising:
   tibolone at a concentration comprised between 1 and 5%, by weight of the pharmaceutical composition;
   a mixture of mannitol and lactose, wherein the weight ratio of the mannitol to the lactose is between 4:1 and 1:1, and wherein the mixture constitutes at least 80% by weight of the pharmaceutical composition;
optionally a starch at a concentration of 10% by weight or less;
optionally an antioxidant at a concentration of between 0.1 and 1% by weight of the pharmaceutical composition; and
optionally a lubricant at a concentration of bet 0.1 and 5% by weight of the pharmaceutical composition.

9. The pharmaceutical composition according to claim 2, wherein the sugar-alcohol is present in the solid dosage form at a concentration of at least 40% by weight.

10. A method of preparing a solid dosage form comprising tibolone at a concentration of between 1 and 5% by weight of the pharmaceutical composition, and a mixture of a sugar-alcohol and a non-sugar-alcohol at a concentration of at least 80% by weight, the method comprising:
mixing tibolone with a sugar-alcohol selected from the group consisting of mannitol, maltitol, sorbitol, xylitol, lactitol, and isomalt, or any mixture thereof, a non-sugar-alcohol diluent selected from the group consisting of: lactose and lactose monohydrate, and optionally further excipients, wherein the weight ratio of the sugar-alcohol to the non-sugar-alcohol diluent is between 4:1 and 1:2; and
formulating the resulting mixture into a solid dosage form.

11. A pharmaceutical composition comprising:
2.5% by weight of tibolone;
86.3% by weight of mannitol;
10% by weight of potato starch;
0.2% by weight of ascorbyl palmitate; and
1% by weight of magnesium stearate.

12. The pharmaceutical composition according to claim 10, wherein the sugar-alcohol is present in the solid dosage form at a concentration of at least 40% by weight.

13. The method according to claim 10, wherein said formulation is prepared by a direct compression procedure, a wet granulation procedure or a dry granulation procedure.

14. The method according to claim 10, wherein said sugar-alcohol is selected from the group consisting of mannitol, maltitol, and xylitol.

15. The method according to claim 10, wherein said mixture comprises mannitol and lactose.

16. The method according to any claim 12, wherein the tibolone is present at a concentration of between 1 and 5% by weight.

17. The method according to claim 10, wherein said composition further comprises a starch at a concentration of 10% by weight or less.

18. The method according to claim 10, wherein said composition further comprises an antioxidant at a concentration comprised between 0.1 and 1% by weight.

19. The method according to claim 10, wherein the composition is in the form of a tablet.

* * * * *

UNITED STATES PATENT AND TRADEMARK OFFICE
CERTIFICATE OF CORRECTION

PATENT NO. : 10,736,907 B2  
APPLICATION NO. : 16/095917  
DATED : August 11, 2020  
INVENTOR(S) : Severine Jaspart Page 1 of 1

It is certified that error appears in the above-identified patent and that said Letters Patent is hereby corrected as shown below:

In the Specification

In Column 1, Line 25, delete "progestonic" and insert --progestogenic--.

In Column 2, Line 4, delete "desintegrant" and insert --disintegrant--.

In Column 2, Line 46, delete "n" and insert --on--.

In Column 3, Line 3, delete "about about" and insert --about--.

In Column 7, Line 31, delete "one)" and insert --one--.

In Column 14, Line 1, delete "25° 0160%" and insert --25° C./60%--.

In the Claims

In Column 22, Line 64, Claim 8, delete "5%," and insert --5%--.

In Column 23, Line 8, Claim 8, delete "bet" and insert --between--.

In Column 24, Line 7, Claim 12, delete "pharmaceutical composition" and insert --method--.

In Column 24, Line 17, Claim 16, delete "any".

Signed and Sealed this  
Twenty-second Day of December, 2020

Andrei Iancu  
*Director of the United States Patent and Trademark Office*